(12) United States Patent
Schuerf et al.

(10) Patent No.: US 7,419,836 B2
(45) Date of Patent: Sep. 2, 2008

(54) DEVICE AND METHOD FOR OBSERVING REACTIONS IN SAMPLES

(75) Inventors: Markus Schuerf, Vachendorf (DE); Harald Gebetsroither, Grodig (AT); Andreas Erlbacher, Abtenau (AT)

(73) Assignee: Tecan Trading AG, Mannedorf (CH)

( * ) Notice: Subject to any disclaimer, the term of this patent is extended or adjusted under 35 U.S.C. 154(b) by 821 days.

(21) Appl. No.: 10/760,829

(22) Filed: Jan. 20, 2004

(65) Prior Publication Data

US 2004/0197926 A1    Oct. 7, 2004

(30) Foreign Application Priority Data

Jan. 21, 2003  (CH) .................................. 0085/03

(51) Int. Cl.
*G01N 21/00*  (2006.01)
(52) U.S. Cl. .................. 436/164; 436/172; 422/82.05; 422/82.08; 422/82.09
(58) Field of Classification Search ............. 422/82.05, 422/82.06, 82.07, 82.08, 82.09, 82.11, 52, 422/67, 100, 82.04, 47, 63, 65; 436/164, 436/50, 172, 501, 518, 47; 356/402, 344, 356/417, 73, 318, 436, 34; 359/159, 204, 359/212, 215, 226, 368, 391; 250/234
See application file for complete search history.

(56) References Cited

U.S. PATENT DOCUMENTS

| | | | | |
|---|---|---|---|---|
| 5,290,513 | A | * | 3/1994 | Berthold et al. ............... 422/52 |
| 5,542,012 | A | | 7/1996 | Fernandes et al. |
| 5,611,994 | A | * | 3/1997 | Bailey et al. .................. 422/52 |
| 5,682,232 | A | * | 10/1997 | Tajima et al. ............... 356/246 |
| 5,784,152 | A | | 7/1998 | Heffelfinger et al. |
| 6,144,455 | A | * | 11/2000 | Tuunanen et al. ........... 356/402 |

(Continued)

FOREIGN PATENT DOCUMENTS

EP    0136002 A2 *  3/1985

(Continued)

*Primary Examiner*—Jill Warden
*Assistant Examiner*—Imran Akram
(74) *Attorney, Agent, or Firm*—Nataro & Michalos P.C.

(57) ABSTRACT

The present invention relates to a device (1) for observing reactions in samples (2), to which a reagent (3) is added, and/or a method which is based on the use of this device. The device includes at least one first optical device (4) for observing samples (2) in the direction of a first optical axis (5) and in a first observation region (6) penetrated by the first optical axis; a first device (7) for receiving receptacles (8) containing samples (2) and for aligning samples in these receptacles in relation to the first optical axis (5); and an injection device (10) for adding liquids (3) to samples (2) and an illumination device (17) for irradiating the samples (2) with excitation light of a first wavelength. In this case, the injection device (10) is preferably positioned between the first optical device (4) and the receptacles (8) and includes at least one injector opening (11) of an injector needle (12) positioned in the observation region (6) of the first optical device (4) and a supply line (13) assigned thereto. The device (1) according to the present invention is characterized in that the injection device (10) for adding liquids (3) to samples (2) includes a tray (24) which is implemented for carrying and positioning the at least one injector needle (12) and its supply line (13).

20 Claims, 2 Drawing Sheets

U.S. PATENT DOCUMENTS 6,146,882 A * 11/2000 Uematsu et al. .......... 435/303.1
6,377,342 B1 * 4/2002 Coeurveille ................ 356/244
6,388,788 B1 * 5/2002 Harris et al. ............... 359/196
6,466,316 B2 * 10/2002 Modlin et al. ............. 356/318
2002/0043626 A1 * 4/2002 Booker et al. ............ 250/459.1

FOREIGN PATENT DOCUMENTS

EP 0803724 10/1997

* cited by examiner

DEVICE AND METHOD FOR OBSERVING REACTIONS IN SAMPLES

RELATED APPLICATIONS

This application claims priority of the Swiss patent application No. 0085/03 filed on Jan. 21, 2003, the disclosure of which is herein incorporated by reference for all purposes.

RELATED FIELD OF TECHNOLOGY

The present invention relates to a device and a method for observing samples to which a reagent is added according to the preamble of independent claims 1 and 16, respectively. In this case, this device for observing reactions in samples includes at least one first optical device for observing samples in the direction of a first optical axis and in a first observation region penetrated by the first optical axis; a first device for receiving receptacles containing samples and for aligning samples in these receptacles in relation to the first optical axis and an injection device for adding liquids to samples. In this case, the injection device includes at least one injector opening of an injector needle positioned in the observation region of the first optical device and an associated supply line.

RELATED PRIOR ART

Devices according to the species, known for many years from the related art, are based on measuring the luminescence of samples admixed with a reagent. Luminescence generally refers to emission of light which is to be attributed to the occurrence of a chemical reaction in a sample. These devices for observing reactions in samples to which a reagent has been added include at least one first optical device for observing samples in the direction of a first optical axis. In addition, such devices include a first device for receiving receptacles containing samples and for aligning samples in these receptacles in relation to the first optical axis and a second device for mutual alignment of the samples and the first optical device along the first optical axis. Using an injection device, liquids and/or reagents are added to the samples provided. The injection device is positioned in this case between the first optical device and the receptacles and includes at least one injector opening of an injector needle positioned in the observation region of the first optical device and a supply line assigned thereto. The injector is thus used for starting or initiating such a reaction which triggers luminescence of the sample. In this case, a specific quantity of a liquid reagent is added using an injector to a liquid sample provided. Liquids such as activation solutions, stop solutions, and the like are referred to as reagents. After the detection and recording of the luminescence triggered by this reaction, the sample is shifted to a second measurement position to trigger and measure fluorescence emitted by the sample. Fluorescence generally refers to emission of light which is to be attributed to the irradiation of a sample with a light source; in this case, the frequency of the excitation light is typically different from the frequency of the fluorescent light emitted by the sample.

The fluorescence and/or luminescence of the samples may be emission of light resulting from the structure of the sample itself. However, it may also be a property added to the samples, as may be generated by staining of the samples with corresponding materials, which are well-known in the related art, or even through known materials which bind to sample molecules using antibodies or ligands. Using the devices known from the related art, it is not possible to track luminescence triggered by the reaction of the sample with the reagent and fluorescence triggered by irradiation of the sample with excitation light simultaneously.

In addition, in the devices known from the related art, the set up and/or replacement of the injectors may only be performed when the housing is open. The injectors and/or injector needles may be damaged during this delicate work.

OBJECT AND SUMMARY OF THE INVENTION

The object of the present invention is therefore to suggest a device, using which the luminescence and/or the fluorescence of samples admixed with a reagent and irradiated using excitation light may be measured and in which the injectors and/or injector needles may be positioned and/or replaced easily.

This object is achieved according to the features as described herein. Advantageous refinements and additional features of the present invention are obtained as also disclosed herein.

Advantages of the present invention include the following:

The entire kinetics of the reaction of a sample to the admixing with a reagent and the intensity and distribution of the luminescence emission connected therewith may be recorded simultaneously with the excitation and measurement of the fluorescence of the sample and without any shift of samples or detectors.

If all of the samples received in the 96, 384, or 1536 wells of a microplate, for example, are to be assayed for fluorescence and luminescence simultaneously, this may be performed in that the microplate must only be moved in relation to the shared optical axis of the device by the distance of two neighboring wells in each case to detect the fluorescence and/or the luminescence. Time-consuming back and forth movement of the microplate from the location of an optical device for detecting the fluorescence to the location of the optical device for detecting the luminescence is dispensed with, which represents a great time savings—particularly for 1536-well microplates.

The injectors and/or injector needles may be removed from the device and placed therein again easily and secure from damage.

Prior to performing experiments, the injectors and/or injector needles may be inspected, cleaned, and tested for their perfect function outside the device and without impairing the device in any way (e.g., through contamination).

The tray for receiving and protecting the injectors and/or injector needles may be used for the purpose of defining the observation region for the luminescence of the samples.

BRIEF DESCRIPTION OF THE DRAWINGS

The device according to the present invention and/or the method according to the present invention will be described in greater detail on the basis of a schematic and exemplary drawing, without this drawing restricting the scope of the present invention.

DETAILED DESCRIPTION OF THE INVENTION

Figure 1:
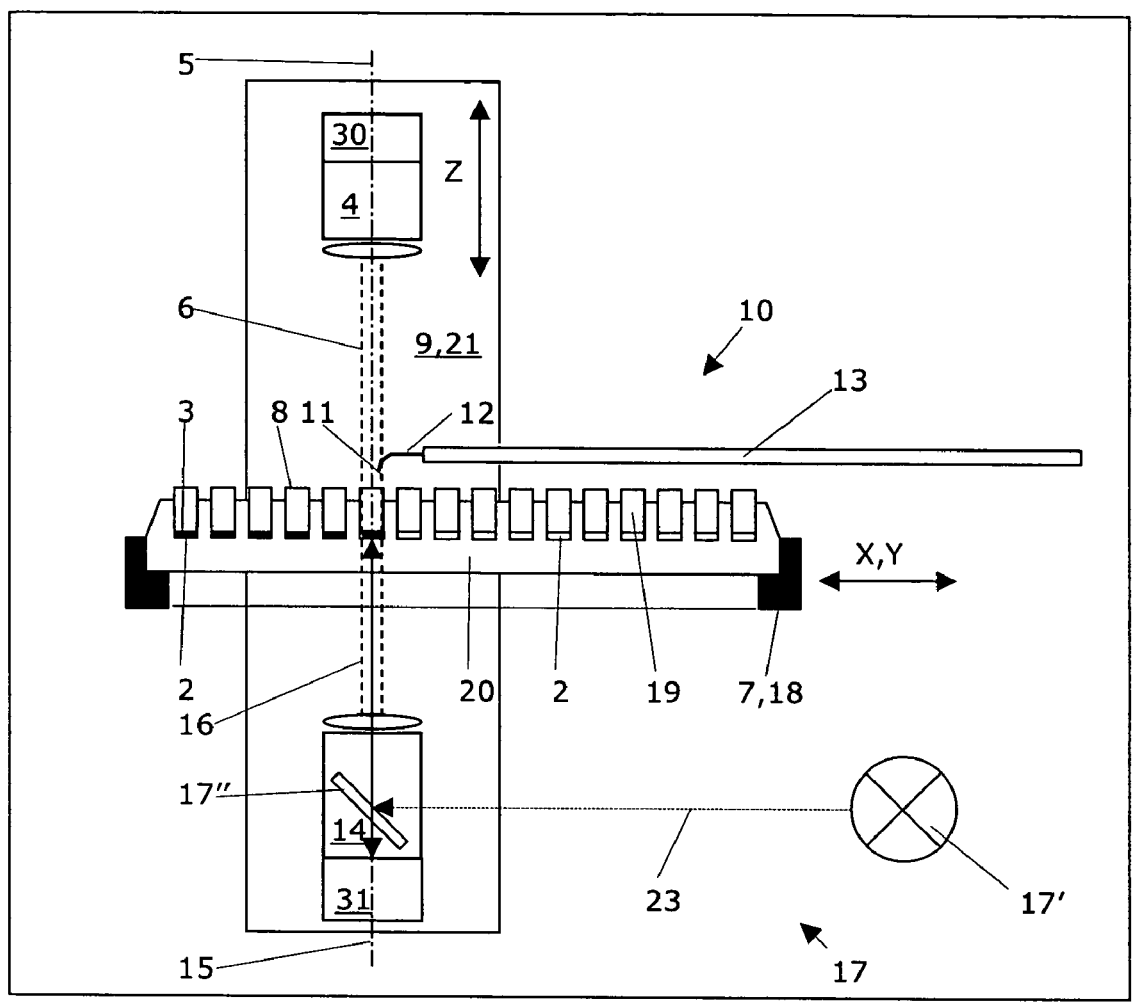
FIG. 1 shows a vertical section through the device according to a first embodiment.

FIG. 1 shows a device 1 for observing reactions in samples 2, to which a reagent 3 is added, according to a first embodiment. This device includes a first optical device 4 for observing samples 2 in the direction of a first optical axis 5 and in a first observation region 6 penetrated by the first optical axis. The observation region 6 preferably precisely corresponds to the inner area of a well of a microplate having 96, 384, or 1536 wells. In addition, the device includes a first device 7 for receiving receptacles 8 containing samples 2 and for aligning samples in these receptacles in relation to the first optical axis 5. Especially preferred receptacles are the microplates already cited, which are aligned essentially horizontally in the device and allow the automatic processing of large numbers of samples. A second device 9 is preferably implemented for mutual alignment of the samples 2 and the first optical device 4 along the first optical axis 5. This first optical axis preferably runs in the vertical Z direction.

An injection device 10 is used for adding liquids 3 to samples 2. This injection device is preferably positioned between the first optical device 4 and the receptacles 8 and includes at least one injector opening 11 of an injector needle 12 and/or an injector positioned in the observation region 6 of the first optical device 4, and a supply line 13 assigned thereto.

The device 1 according to the present invention preferably also includes a second optical device 14 for observing the samples 2 in the direction of a second optical axis 15 and in a second observation region 16, penetrated by the second optical axis. In addition, the device 1 according to the present invention includes an illumination device 17 for irradiating the samples 2 with excitation light of a first wavelength. For this purpose, the light of a flashlamp 17' is preferably deflected onto the sample 2 via a dichroic mirror 17" positioned in the beam path of the second optical axis 15. The fluorescent light of the sample then reaches the fluorescence detector 31 of the second optical device 14 through the dichroic mirror 17". The injection device 10 and the receptacle 8 having the samples 2 are positioned between the two optical devices 4, 14. The two observation regions 6, 16 are essentially coincident and the two optical axes 5, 15 run essentially parallel to one another in opposite directions. The two optical axes 5, 15 are preferably identical to one another and run essentially vertically. A device 1 in which the first optical device 4 is implemented for detecting a luminescence emitted by the sample 2 and the second optical device 14 is implemented for detecting a fluorescence emitted by the sample 2 is especially preferred.

The first device 7 for receiving receptacles 8 containing samples 2 and for aligning samples 2 in these receptacles 8 in relation to the first optical axis 5 includes a receiver 18 for carrying receptacles 8. For this purpose, this receiver is implemented as movable in a horizontal plane in the X and Y directions. This motion in an essentially horizontal X-Y field is preferably performed using a receiver device similar to a mechanical stage and through a motorized drive (not shown). The receiver 18 is implemented in the region of the samples in such a way that the excitation light may reach the samples from below and the fluorescent light of the samples thus triggered may reach the second optical device 14 having the fluorescence detector 31.

The device 1 preferably includes a second device 9 for mutual alignment of the samples 2 and the first optical device 4 along the first optical axis 5 of a suspension 21. The first optical device 4 is attached thereto so it is movable in a vertical Z direction. As FIG. 1 shows, the first optical device 4 is therefore movable in the Z direction (arrow) and positioned above the receiver 18 for carrying receptacles 8, while the second optical device 14 is preferably immovably fixed and positioned below the receiver 18.

Figure 2:
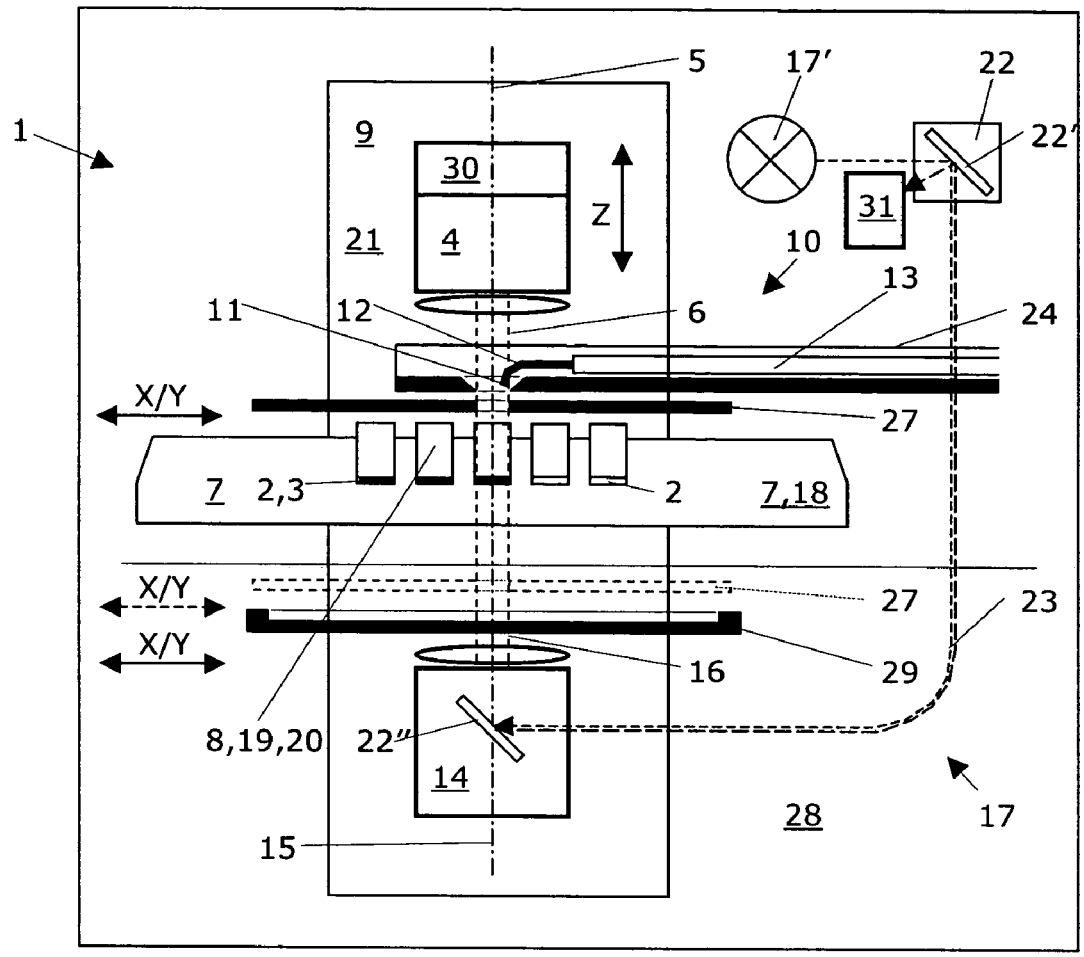
FIG. 2 shows a vertical section through a device according to a second embodiment.
Figure 3:
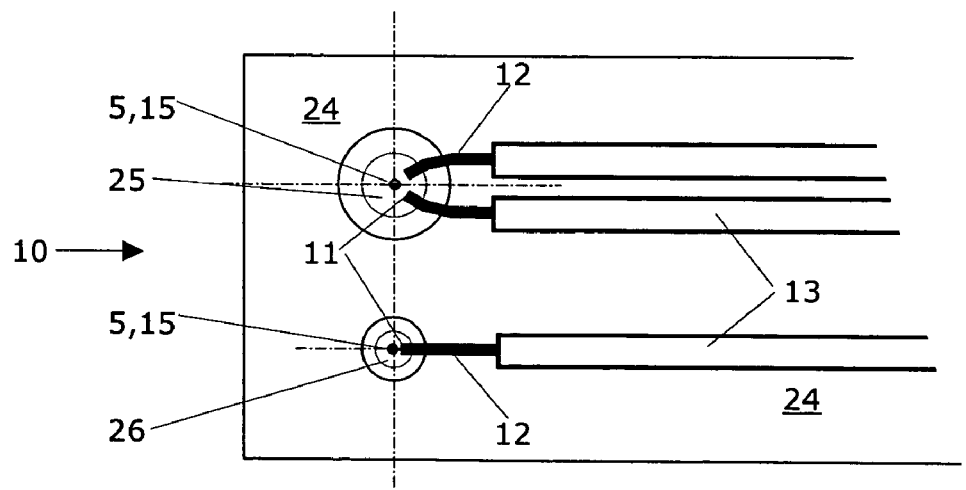
FIG. 3 shows a top view of the injectors and their accommodation in the second embodiment.

An especially preferred, second embodiment of the present invention is shown in FIGS. 2 and 3. Besides the elements of the first embodiment already described, the injection device 10 of this device for adding liquids 3 to samples 2 includes a tray 24, which is implemented for carrying and positioning at least one injector needle 12 and its supply line 13. The injection device 10 especially preferably has three injector needles 12, each having an injector opening 11 and a supply line 13. In this case, two injector openings 11 are positioned next to one another in a first observation region 25 tailored to a 96-well microplate and the third injector opening 11 is positioned in a second observation region 26 tailored for a 384-well microplate (cf. top view in FIG. 3).

Alternatively to the illustration in FIG. 3, two injector needles 12 may also be positioned next to one another in a second observation region 26 tailored for a 384-well microplate and/or more or less than three injector needles 12 (e.g., 1, 2, or 4 needles) may be positioned on a tray 24. In addition, three or four injector needles 12, for example, may be positioned in one of the observation regions 25, 26, or each in multiple observation regions (not shown).

This second embodiment preferably includes an illumination device 17 having a beam splitter slide 22 and an optical fiber 23, via which the beam splitter slide 22 is connected to the second optical device 14 (cf. FIG. 2). This illumination device includes a light source 17' (e.g., a flashlamp), whose excitation light is preferably deflected onto the sample 2 via a mirror 22" positioned in the beam path of the second optical axis 15. The two observation regions 25, 26 are defined by openings in the tray 24 of the injection device 10 and/or by screens 27 positioned below the tray 24. As shown in FIG. 2, the screens 27 may be implemented so they may be moved by motors in the X or Y directions and positioned either between tray 24 and samples 2 (shown solid) or between receiver 18 and second optical device 14 (shown dashed). A screen attached to the bottom of the tray 24 itself (not shown) may also be provided or the use of screens may be dispensed with completely.

The tray 24 of the injection device 10 is preferably connected to the first optical device 4 and attached thereto so its height is adjustable in this second embodiment of the device 1 according to the present invention. The tray 24 of the injection device 10 may also be attached to a housing part 28 of the device 1 and attached so its height is adjustable in relation thereto. In this case, the tray 24 of the injection device 10—for setting the height of the injection device 10 using the first optical device 4—is preferably elastically attached to the first optical device 4 and to the housing part 28 of the device 1. An especially user-friendly variation of the device 1 provides that the tray 24 having the injector needles 12 is attached to the housing part 28 of the device 1 so it may be snapped in and/or pulled out. Preferably, the tray 24 is attached to the first optical device 4 and is adjustable together with it in the Z direction.

The device 1 according to all of the embodiments described thus far preferably includes a protective shield 29, which is movably positioned between the injection device 10 and the second optical device 14—e.g., in the X direction or in the Y direction—and covers the second optical device 14 in one position. This has the advantage that a protective shield 29 may always be positioned over the second optical device 14 when a replacement of the receptacles 8 and/or a microplate 20 is performed. By using this protective shield, unintended dripping of liquid out of the injector openings 11 onto the sensitive second optical device 14 is successfully prevented.

In order that no components of the device 1 may have an interfering influence on the detection of the fluorescence and/or luminescence, the injector needles 12 and/or at least the parts thereof extending into an observation region 25, 26 and the two optical devices 4, 14 preferably include materials and/or have surfaces which are themselves neither luminescent nor fluorescent. Such surfaces may have appropriate coatings having Teflon®, for example, (trademark of DuPont, Wilmington, USA) or may also be mechanically roughened (e.g., brushed or sandblasted). In addition, the injection device 10 may include at least three injector needles 12 and the tray 24 and/or at least the part thereof defining an observation region 25, 26 may include materials and/or have surfaces which are neither luminescent nor fluorescent.

In a method for observing reactions in samples 2 using a device 1 according to the first or second embodiment or an embodiment differing therefrom, which includes at least one first optical device 4 for observing samples 2 in the direction of a first optical axis 5 and in an observation region 6 penetrated by the first optical axis 5, a first device 7 for receiving receptacles 8 containing samples 2 and for aligning samples 2 in these receptacles 8 in relation to the first optical axis 5, preferably a second device 9 for mutual alignment of the samples 2 and the first optical device 4 along the first optical axis 5, and an injection device 10 for adding liquids 3 to samples 2, the injection device 10 preferably being positioned between the first optical device 4 and the receptacles 8 and including at least one injector opening 11 of an injector needle 12 positioned in the observation region 6 of the first optical device 4 and an associated supply line 13, it is provided according to the present invention that the device 1 preferably includes a second optical device 14 for observing the samples 2 in the direction of a second optical axis 15 and in a second observation region 16 penetrated by the second optical axis 15, and an illumination device 17 for irradiating the samples 2 with excitation light of a first wavelength, the injection device 10 and the receptacle 8 having the samples 2 being positioned between the two optical devices 4, 14 and the two observation regions 6, 16 being essentially coincident and the two optical axes 5, 15 running essentially parallel to one another in opposite directions.

The method according to the present invention includes the following operating steps:

adding a reagent 3 to a sample 2 using the injection device 10 of the device 1, which includes a tray 24, implemented for carrying and positioning the at least one injector needle 12 and its supply line 13, for adding liquids 3 to samples 2 irradiating this sample 2 with excitation light of a first wavelength using the illumination device 17 simultaneous recording of the luminescence and the fluorescence of the sample 2 using the two optical devices 4, 14 recording the luminescence or the fluorescence of the sample 2 with one of the two optical devices 4, 14.

In accordance with this use of the device, it may also be provided that a screen 27 is positioned between injection device 10 and samples 2 in such a way that the two observation regions 6, 16 are reduced to an observation region 25 tailored to a 96-well microplate or to an observation region 26 tailored for a 384-well microplate. A motorized, movable screen is especially preferred, using which one may switch back and forth automatically—e.g., between the observation regions 25 and 26.

Devices and methods in which the individual operating steps, such as the insertion/removal of receptacles 8 into/out of a receiver 18, positioning of the samples in the X and/or Y direction in relation to the optical axis 5, 15 of the detectors; the mutual positioning of samples 2 and luminescence detector 30 of the first optical device 4 in the Z direction; the adding of liquids using one or more injectors and/or injector needles 12; the movement of the beam splitter slide 22 having a mirror 22' into a position in which excitation light is deflected into the optical fiber 23 and then via a further mirror 22" positioned in the beam path of the second optical axis 15 onto the sample 2; the emission of light flashes using the light source 17' of the illumination device 17; the detection of the fluorescence emitted by the sample 2, which reaches a fluorescence detector 31 via the mirror 22" and the optical fiber 23 and the mirror 22'; the detection of the luminescence emitted by the sample 2, which reaches a luminescence detector 30, and the recording, processing, and analysis and/or output of the corresponding signals output by the detectors, may be controlled by a computer and executed automatically and/or driven by a motor are especially preferred. Such devices preferably include such a computer or are connectable to a computer equipped with the corresponding capabilities. Such devices may also include additional detectors which are suitable for detecting absorbance, fluorescence, or luminescence values, for example.

The reference numbers identify corresponding elements of the device in all figures, even if they are not expressly described. Combinations of elements of the devices described are included in the extent of the present invention.

What is claimed is:

1. A device for observing reactions in samples, to which a reagent is added, the device comprising:
    a housing part (28);
    a first optical device (4) having a luminescence detector (30) for observing samples (2) in the direction of a first optical axis (5) and in a first observation region (6) penetrated by the first optical axis (5);
    a second optical device (14) having a fluorescence detector (31) for observing samples (2) in the direction of a second optical axis (15) and in a second observation region (16) penetrated by the second optical axis (15),
    wherein the two optical axes (5), (15) run in a substantially vertical Z direction and parallel to one another in opposite directions; and
    wherein the two observation regions (6), (16) are substantially coincident for detection of a luminescence and a fluorescence emitted by the sample (2),
    a first device (7) for receiving receptacles (8) containing samples (2) and for aligning samples in the receptacles in relation to the first and the second optical axes (5), (15);
    an injection device (10) for adding liquids (3) to samples (2),
    wherein the injection device (10) includes at least one injector opening (11) of an injector needle (12) positioned in the first or in the second observation region (6), (16) and at least one supply line (13) assigned to the injection needle;
    an illumination device (17) for irradiating samples (2) with excitation light of a first wavelength,
    wherein the injection device (10) includes a tray (24) for carrying and positioning the at least one injector needle (12) and its supply line (13); the tray (24) being directly attached to the housing part (28) of the device, and the tray (24) having the at least one injector needle (12).

2. The device according to claim 1, wherein the tray comprises a snap-in-and-pull-out tray.

3. The device according to claim 1, including a second device (9) for mutual alignment of the samples and the first optical device along the first axis.

4. The device (1) according to claim 3, wherein the second device (9) includes a suspension (21) for mutual alignment of the samples (2) and the first optical device (4) along the first optical axis (5), to which the first optical device (4) is attached so it is movable in a vertical Z direction.

5. The device according to claim 4, wherein the tray is attached to the first optical device so that the height of the tray is adjustable together with the height of the first optical device in the Z-direction.

6. The device according to claim 5, wherein the tray is attached to the first optical device and to the housing part of the device, each by an elastic connection.

7. The device (1) according to claim 1, wherein the two observation regions (25, 26) are defined by at least one of: openings in the tray (24) of the injection device (10); and by screens (27) positioned below the tray (24).

8. The device according to claim 1, wherein the two optical axes are identical to one another.

9. The device according to claim 1, wherein the first device (7) for receiving receptacles containing samples and for aligning samples in the receptacles in relation to the first and the second optical axis includes a receiver (18) for carrying receptacles which is movable in a horizontal plane in the X and Y directions.

10. The device according to claim 1, wherein the receptacles (8) are wells (19) of microplates (20) in which samples (2) are received, the microplates (20) being aligned substantially horizontally.

11. The device (1) according to claim 1, wherein the first optical device (4) is positioned above the receiver (18) for carrying receptacles (8) and the second optical device (14) is positioned below the receiver.

12. The device (1) according to claim 1, wherein the illumination device (17) includes a beam splitter slide (22) and an optical fiber (23), by which the beam splitter slide is connected to the second optical device (4).

13. The device (1) according to claim 1, including a protective shield, which is movably between the injection device and the second optical device and covers the second optical device in one position.

14. The device according to claim 1, wherein the two optical devices (4, 14) at least one of: include materials; and have surfaces which are neither luminescent nor fluorescent.

15. The device according to claim 1, wherein at least part of the injector needles (12) include materials or have surfaces which are neither luminescent nor fluorescent.

16. A method for observing reactions in samples using a device according to claim 1, which comprises:
a housing part (28);
a first optical device (4) having a luminescence detector (30) for observing samples (2) in the direction of a first optical axis (5) and in a first observation region (6) penetrated by the first optical axis (5);
a second optical device (14) having a fluorescence detector (31) for observing samples (2) in the direction of a second optical axis (15) and in a second observation region (16) penetrated by the second optical axis (15),
wherein the two optical axes (5), (15) run substantially in a vertical Z direction and parallel to one another in opposite directions; and wherein the two observation regions (6), (16) are substantially coincident for detection of a luminescence and a fluorescence emitted by the sample (2),
a first device (7) for receiving receptacles (8) containing samples (2) and for aligning samples in the receptacles in relation to the first and the second optical axis (5), (15);
an injection device (10) for adding liquids (3) to samples (2),
wherein the injection device (10) includes at least one injector opening (11) of an injector needle (12) positioned in the first or in the second observation region (6), (16) and at least one supply line (13) assigned to the injection needle, and wherein the injection device (10), for adding liquids to samples, includes a tray (24) for carrying and positioning the at least one injector needle (12) and its supply line (13); the tray (24) being directly attached to the housing part (28) of the device, and the tray (24) having the at least one injector needle (12);
an illumination device (17) for irradiating samples (2) with excitation light of a first wavelength,
wherein the method comprises the steps of:
a) admixing a sample with a reagent using the injection device,
b) irradiating the sample with excitation light of a first wavelength using the illumination device, and
c) recording the luminescence and the fluorescence of the samples simultaneously using the two optical devices.

17. The method according to claim 16, wherein the injection device (10) and the receptacles (8) having the samples (2) are positioned between the two optical devices (4, 14).

18. The method according to claim 16, in which a screen (27) is positioned between the injection device (10) and samples (2) in such a way that an observation region (6) is reduced to an observation region (25) tailored for a 96-well microplate or to an observation region (26) tailored for a 384-well microplate.

19. The method according to claim 16, in which a screen (27) is positioned between the injection device (10) and samples (2) in such a way that both observation regions (6, 16) are reduced to an observation region (25) tailored for a 96-well microplate or to an observation region (26) tailored for a 384-well microplate.

20. The method according to claim 16, in which a protective shield (29) is always positioned over the second optical device (14) when a replacement of the receptacle (8) or a microplate (20) is performed.

* * * * *

UNITED STATES PATENT AND TRADEMARK OFFICE
CERTIFICATE OF CORRECTION

PATENT NO. : 7,419,836 B2
APPLICATION NO. : 10/760829
DATED : September 2, 2008
INVENTOR(S) : Markus Schuerf, Harald Gebetsroither and Andreas Erlbacher It is certified that error appears in the above-identified patent and that said Letters Patent is hereby corrected as shown below:

Title Page, Item (74) should read as:

-- (74) Attorney, Agent, or Firm - Notaro & Michalos P.C. --.

Signed and Sealed this

Ninth Day of December, 2008

JON W. DUDAS
*Director of the United States Patent and Trademark Office*